United States Patent
Nguyen et al.

(10) Patent No.: US 8,236,289 B2
(45) Date of Patent: Aug. 7, 2012

(54) LIP GLOSS

(75) Inventors: Lethu T. Nguyen, Colonia, NJ (US);
Yinli Wang, Ramsey, NJ (US); Domnica Cernasov, Ringwood, NJ (US); Ralph Macchio, Sparta, NJ (US); Salvatore J. Barone, Staten Island, NY (US)

(73) Assignee: Coty S.A.S., Paris (FR)

( * ) Notice: Subject to any disclaimer, the term of this patent is extended or adjusted under 35 U.S.C. 154(b) by 1087 days.

(21) Appl. No.: 12/140,039

(22) Filed: Jun. 16, 2008

(65) Prior Publication Data
US 2009/0060857 A1    Mar. 5, 2009

Related U.S. Application Data

(63) Continuation-in-part of application No. 12/138,633, filed on Jun. 13, 2008.

(60) Provisional application No. 60/944,347, filed on Jun. 15, 2007.

(51) Int. Cl.
*A61Q 1/04* (2006.01)

(52) U.S. Cl. .......................... 424/64; 424/401

(58) Field of Classification Search ............ None
See application file for complete search history.

(56) References Cited

U.S. PATENT DOCUMENTS

| | | | |
|---|---|---|---|
| 5,744,129 A * | 4/1998 | Dobbs et al. | 424/61 |
| 2006/0204460 A1 | 9/2006 | Takeda et al. | |
| 2006/0269508 A1 | 11/2006 | Trejo | |
| 2007/0025941 A1 * | 2/2007 | Robert et al. | 424/64 |
| 2007/0071980 A1 | 3/2007 | Kamei et al. | |
| 2007/0104662 A1 | 5/2007 | Satonaka et al. | |
| 2009/0047229 A1 | 2/2009 | Nguyen et al. | |

FOREIGN PATENT DOCUMENTS

| | | |
|---|---|---|
| KR | 5013680 | 2/2005 |
| WO | WO-2008156723 A2 | 12/2008 |
| WO | WO-2008156723 A3 | 2/2009 |
| WO | WO-22009035484 A1 | 3/2009 |

OTHER PUBLICATIONS

"U.S. Appl. No. 12/138,633, Restriction Requirement mailed Oct. 7, 2011", 8 pgs.
"International Application No. PCT/US2008/007423, Search Report mailed Dec. 30, 2008", 3 pgs.
"International Application No. PCT/US2008/007423, Written Opinion mailed Dec. 30, 2008", 5 pgs.
"International Application No. PCT/US2008/007479, Search Report mailed Dec. 30, 2008", 3 pgs.
"International Application No. PCT/US2008/007479, Written Opinion mailed Dec. 30, 2008", 5 pgs.

* cited by examiner

*Primary Examiner* — Jyothsna Venkat
(74) *Attorney, Agent, or Firm* — Schwegman, Lundberg & Woessner, P.A.

(57) ABSTRACT

Embodiments of inventive subject matter described herein include a lip gloss comprising: a sugar gel matrix that includes stearoyl inulin and an ester or ether of formula R(1) COOR(2) in which R(1) is a residue of a fatty acid including from 6 to 29 carbon atoms and R(2) is a hydrocarbon-comprising chain comprising from 3 to 30 carbon atoms, entrapped in the stearoyl inulin sugar gel matrix; a gel comprising hydrogenated polyisobutene; and a gel comprising fumed silica dimethyl silicate in C(15-19) Hydrocarbon.

18 Claims, 2 Drawing Sheets

LIP GLOSS

RELATED APPLICATION

This application is a continuation in part of U.S. patent application Ser. No. 12/138,633, filed Jun. 13, 2008, which application claims priority under 35 U.S.C. 119(e) of U.S. Provisional Patent Application Ser. No. 60/944,347, filed Jun. 15, 2007, which applications are incorporated herein by reference.

Inventive subject matter described herein relates to lip gloss embodiments; method embodiments for making a lip gloss, method embodiments for packaging lip gloss and lip gloss system embodiments.

COPYRIGHT

A portion of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever. Copyright 2008, Coty SAS, Inc.

BACKGROUND

Women have adorned their lips for thousands of years. Ancient Egyptians used henna to paint their lips. Thirteenth Century affluent women donned pink lipstick. During the French Restoration in the 18th century, red rouge and lipstick were used to give the impression of a healthy, fun-loving spirit. Women in Victorian England did not use lipstick but did add sheen to their lips with a clear pomade. In America in the 1920's, women applied red lipstick to their lips. It was in the 1920's that lip gloss was introduced into the marketplace.

SUMMARY

One embodiment of a lip gloss includes a sugar gel matrix that includes stearoyl inulin and an ester or ether of formula R(1) COOR(2) in which R(1) is a residue of a fatty acid including from 6 to 29 carbon atoms and R(2) is a hydrocarbon-comprising chain comprising from 3 to 30 carbon atoms, entrapped in the stearoyl inulin sugar gel matrix; a gel comprising hydrogenated polyisobutene; and a gel comprising fumed silica dimethyl silicate in C(15-19) hydrocarbon.

Another embodiment includes a method for making a lip gloss. The method includes blending the following three gels: a sugar gel matrix that includes stearoyl inulin and an ester or ether of formula R(1) COOR(2) in which R(1) is a residue of a fatty acid including from 6 to 29 carbon atoms and R(2) is a hydrocarbon-comprising chain that includes from 3 to 30 carbon atoms, entrapped in the stearoyl inulin sugar gel matrix; a gel comprising hydrogenated polyisobutene; and a gel comprising fumed silica dimethyl silicate in C(15-19) hydrocarbon; and adding a colorant to the blend.

One other embodiment includes a lip gloss system. The lip gloss system includes a gel system comprising: sugar gel matrix that includes stearoyl inulin and an ester or ether of formula R(1) COOR(2) in which R(1) is a residue of a fatty acid including from 6 to 29 carbon atoms and R(2) is a hydrocarbon-comprising chain comprising from 3 to 30 carbon atoms, entrapped in the stearoyl inulin sugar gel matrix; a gel comprising hydrogenated polyisobutene; a gel comprising fumed silica dimethyl silicate in C(15-19) hydrocarbon; and packaging for packaging the gel system.

IN THE FIGURES

To depict the manner in which the embodiments are obtained, a more particular description of embodiments briefly described above will be rendered by reference to exemplary embodiments that are illustrated in the appended drawings. Understanding that these drawings depict only typical embodiments that are not necessarily drawn to scale and are not therefore to be considered to be limiting of its scope, the embodiments will be described and explained with additional specificity and detail through the use of the accompanying drawings in which.

DETAILED DESCRIPTION

Figure 1:
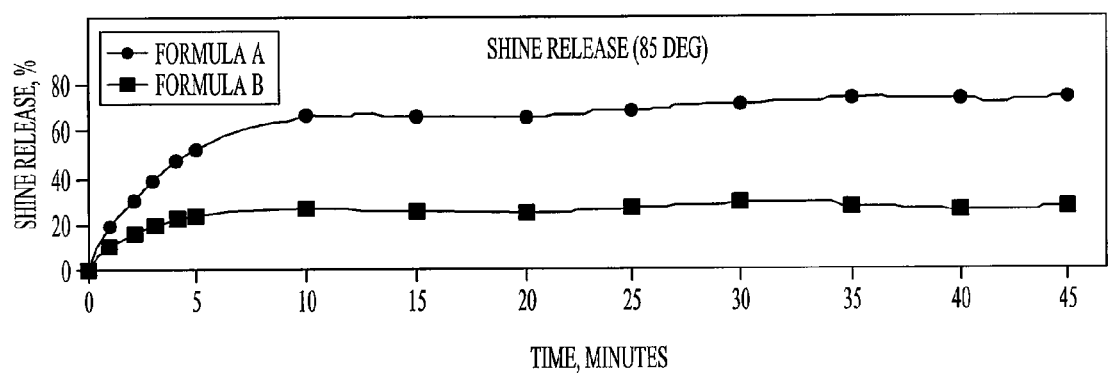
FIG. 1 illustrates graphically, a comparison of shine intensity and duration of one lip gloss embodiment of inventive subject matter described herein and a prior art lip gloss formulation.

Although detailed embodiments are disclosed herein, it is to be understood that the disclosed embodiments are merely exemplary of the invention that may be embodied in various and alternative forms. Specific structural and functional details disclosed herein are not to be interpreted as limiting, but merely as a basis for teaching one skilled in the art to variously employ the aneurysm treatment system embodiments. Throughout the drawings, like elements are given like numerals.

Referred to herein are trade names for materials including, but not limited to, polymers and optional components. The inventors herein do not intend to be limited by materials described and referenced by a certain trade name. Equivalent materials such as those obtained from a different source under a different name or catalog (reference) number to those referenced by trade name, may be substituted and used in the methods described and claimed herein. All percentages and ratios are calculated by weight unless otherwise indicated. All percentages are calculated based on the total composition unless otherwise indicated. All component or composition levels are in reference to the active level of that component or composition, and are exclusive of impurities, for example, residual solvents or by-products, which may be present in commercially available sources One embodiment of lip gloss described herein includes a sugar gel matrix of stearoyl inulin; and an ester or ether of formula R(1) COOR(2) in which R(1) is a residue of a fatty acid including from 6 to 29 carbon atoms and R(2) is a hydrocarbon-including chain that includes from 3 to 30 carbon atoms, entrapped in the sugar gel matrix. The lip gloss gel also includes a gel of fumed silica dimethyl silicate in a C(15-19) hydrocarbon. As used herein, "gel" refers to a two-phase colloidal system that includes a liquid and a solid in the form of a thickened liquid, semi-solid or solid. A gel also refers to a composition that is either physically cross-linked by virtue of entangled polymer chains or by development of associative networks or insoluble domains or is chemically cross-linked by virtue of covalent bonds such that the gel swells, but does not dissolve, in the presence of liquid. A gel typically is obtained by use of a gelling agent. The term "gelling agent" as used herein refers to a polymer dispersed in any suitable liquid, semi-solid, or solid material.

The term "polymer" used herein includes both homopolymer and copolymer. A homopolymer is a polymer obtained by polymerizing one type of monomer, whereas a copolymer is a polymer obtained by polymerizing two or more types of monomers. The term, "block copolymer," refers to a copolymer in which like monomer units occur in relatively long, alternate sequences on a chain. The term "gel composition" as used herein refers to a gelling agent dispersed, dissolved, or swelled in a suitable liquid, semi-solid, or solid material. The term "two-phase gel composition" as used herein refers to a two component system in which one component is a gelled component and the second component is a solvent. The use of the term "two-phase gel composition" is not intended to require that the gel composition have two separate physical phases. As used herein, the term "two-phase gel composition" may be homogenous; i.e., a single phase. In some embodiments, the two-phase gel composition does not separate back into the individual components used to make the two-phase gel composition. In other embodiments, the two-phase gel composition may have two, three, four, five or more phases.

As used herein, the term "opaque" refers to the optical state of a medium whose molecular aggregation is such that light cannot pass through the medium. Therefore, light transmission through an opaque medium is substantially close to zero. The term "transparent" refers to the optical state of a medium through which light can pass through so that an object can be seen through the medium. As used herein, the term "transparent" includes any optical state which is not opaque. A medium is considered transparent even if only a small fraction of light passes through the medium. Thus, a clear gel and a translucent gel are considered transparent.

In one embodiment, the lip gloss includes three different gels, which are as follows:
  Diisostearyl Malate in Stearoyl Inulin
  Silica Dimethyl Silicate in C(15-19) alkane
  Hydrogenated Polyisobutene.

While diisostearyl malate is described, it is understood that other esters and ethers are suitable for use in the formulation embodiments described herein. These esters and ethers include purcellin oil (cetostearyl octanoate), isopropyl myristate, 2-ethylhexyl palmitate, 2-octyldodecyl stearate, isostearyl isostearate, arachidyl propionate or 2-octyldodecyl benzoate; hydroxylated esters, such as isostearyl lactate, octyl hydroxyl stearate, octyldodecyl hydroxyl stearate, triisocetyl citrate; or polyol esters, such as propylene glycol dioctanoate, neopentyl glycol diheptanoate, diethylene glycol diisononanoate and pentaerythritol esters; fatty alcohols having from 12 to 26 carbon atoms, such as octyldodecanol, 2-butyloctanol, 2-hexyldecanol, 2-undecylpentadecanol, oleyl alcohol or cetyl alcohol, isononyl isononanoate, C(12-15) alkyl benzoates, isopropyl myristate, 2-ethylhexyl palmitate, alkyl octanoates, polyalkyl octanoates, decanoates ricinoleates, hydroxylated esters such as isostearyl lactate and pentaerythritol esters. Optionally, the synthetic ethers include from 10 to 40 carbon atoms, or their mixtures.

Comparative testing was performed of an inventive lip gloss formulation embodiment, Formula A, and a prior art formulation, Formula B. These formulas as shown as follows:

EXAMPLE 1

Comparative Test

| Component | Formula A (% by weight) | Formula B (Prior Art) (% by weight) |
|---|---|---|
| Phase A, Pre-made gel | | |
| Diisostearyl Malate | 9.35 | |
| Stearoyl Inulin | 1.15 | |
| Phase B, Pre-made gel | | |
| C(15-19) alkane | 9.24 | |
| Silica Dimethyl Silicate | 1.26 | |
| Phase C | | |
| Hydrogenated Polyisobutene gel | 27.00 | — |
| Polybutene | 32.00 | 32.00 |
| Polyethylene | 1.00 | 1.50 |
| Vp/hexadecane copolymer | 4.00 | 4.00 |
| Diisopropyl Dimer dilinoleate | 4.80 | 17.30 |
| Preservatives | 0.10 | 0.10 |
| Polyisobutene | — | 20.00 |
| Octyldodecanol, disteardimonium Hectorite, Porpylene Carbonate | — | 15.00 |
| Pigments | 0.10 | 0.10 |
| Mica | 10.00 | 10.00 |

Formula A is one embodiment of inventive subject matter described herein and includes pre-made gels. Formula B is a prior art lip gloss formulation and is free of pre-made gels.

Figure 2:
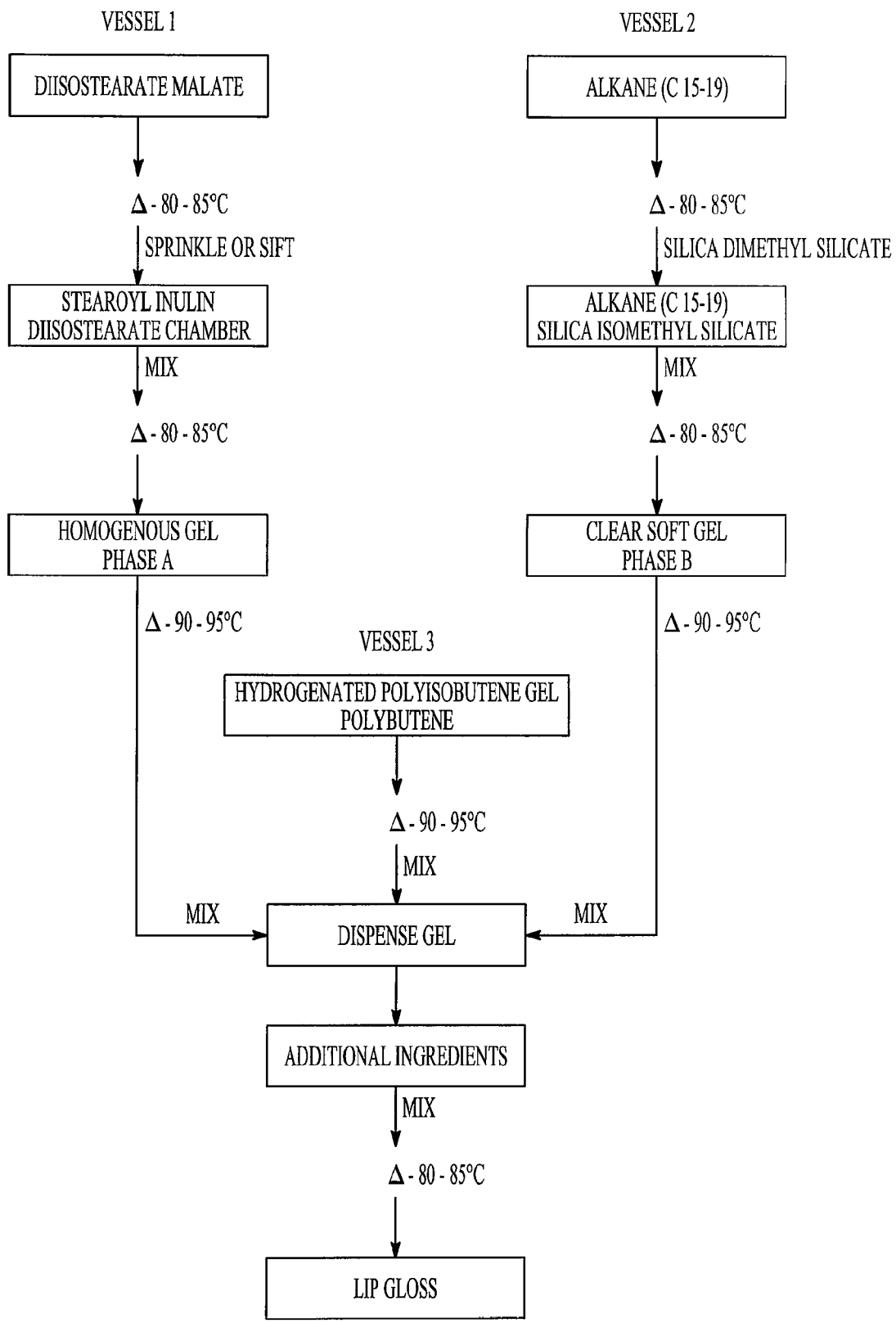
FIG. 2 illustrates schematically, a process embodiment of the invention.

In one embodiment, shown schematically in FIG. 2, the pre-made gels were prepared in two separate vessels, a vessel 1 and a vessel 2. Diisostearate malate was introduced into vessel 1 and was heated to 80 to 85 degrees Centigrade. Stearoyl inulin was sprinkled or sifted into vessel 1, and a resulting mixture was homo-mixed at moderate speed at 80-85 degrees Centigrade to obtain a homogeneous gel. An alkane, C(15-19) was added to vessel 2 and was heated to 80-85 degrees Centigrade. Silica dimethyl silicate was added to vessel 2 and mixed at moderate speed by homo-mixing, at 80-85 degrees Centigrade until a clear soft gel was formed.

In a third vessel, hydrogenated polyisobutene gel and polybutene were combined and heated to 90-95 degrees Centigrade. The heated mixture was mixed at moderate speed until the hydrogenated polyisobutene gel was completely dispersed.

The pre-made gel, Phase A, was added to the third vessel at 90-95 degrees Centigrade, and was mixed. The pre-made Phase B, was added to the third vessel at 90-95 degrees Centigrade, and was mixed well. Mixing was continued until homogeneity of the mixture was ensured. Remaining ingredients of Phase C were added, except pigments and powder, at a temperature of 90-95 degrees Centigrade. Mixing was continued to ensure that waxes were completely melted and homogeneous. The temperature of the mixture was lowered to 85-90 degrees Centigrade and pigments were added. Mixing was continued to ensure that pigments were completely dispersed. Temperature of the mixture was maintained at 85-90 degrees Centigrade. Mica was added and mixed. The mixture was drop batched at 80-85 degrees Centigrade.

The shine intensity and duration of Formula A and Formula B lipglosses were measured by using a Tri gloss Meter, manufactured by Tricor Systems, Inc., of Elgin, Ill., at 85 degrees. A graph, shown in FIG. 1, illustrates that Formula A releases shine with a greater intensity than released by prior art Formula B. In addition, the shine intensity is longer lasting compared to the shine of prior art Formula B. Consumer testing also showed an improved duration of shine renewal and comfort wear. In one consumer test, 80% of the testers felt that the shine for Formula A was either extremely or definitely renewable versus 40% for Formula B.

Consumer testing showed that 40% of testers noted an increase in shine three hours after application of an inventive lip gloss embodiment described herein while no testers having the prior art lip gloss noted an increase in shine after three hours. Eighty percent of testers felt that the shine for the inventive lip gloss was extremely or definitely renewable while 40% of the testers felt that the prior art lip gloss was renewable.

The consumer testing showed that the inventive lip gloss embodiment renewed its shine for a longer period of time than the prior art lip gloss. Shine renewal for the inventive lip gloss lasted until the test was terminated, four hours after application. Shine renewal for the prior art lip gloss lasted up to 2 hours after application. Shine renewal was more pronounced for the inventive lip gloss at these time points: 1 minute, 5 minutes, 30 minutes, 1 hour, 2 hours, 3 hours, and 4 hours.

Lip gloss formulations described herein include features of "time release" of shine and comfort wear that extend the shine and comfort wear features beyond those of conventional lip gloss formulations. It is believed that these features are related to the pre-made gels. Once applied to lips, the lip gloss imparts a shine that is continuously released on a lip due to the super shiny ester Diisostearyl Malate and similar materials, entrapped in the sugar gel matrix of Stearoyl Inulin. In addition, the gel of fumed Silica Dimethyl Silicate in the C(15-19) Hydrocarbon, aids in increasing the shine, moisturizing the lip and providing comfort wear. The Hydrogenated Polyisobutene gel provides the lip gloss formulations described herein with desired texture.

One other embodiment of the lip gloss is as follows:
Shine Renewal Lipgloss
Diisostearyl Malate 4.45
Stearoyl Inulin 0.55
C15-19 alkane 17.60
Silica Dimethyl Silylate 2.40
Hydrogenated Polyisobutene (and) Ethylene/Propylene/Styrene Copolymer (and) Butylene/Ethylene/StyreneCopolymer 25.00
Polybutene 30.00
VP/Hexadecene Copolymer 3.50
Polyethylene 1.00
Propyl Paraben 0.10
D&C Red No. 7 Ca Lake 0.60
Iron Oxide Red 1.00
FD&C Yellow No. 6 A1 Lake 0.60
Titanium Dioxide 1.00
Mica 3.50
Boron Nitride 1.00
Mica and Titanium 3.00
Diisopropyl Dimer Dilinoleate 4.40
Fragrance 0.30

GENERAL COMMENTS

In the detailed description, reference is made to specific examples by way of drawings and illustrations. These examples are described in sufficient detail to enable those skilled in the art to practice the inventive subject matter, and serve to illustrate how the inventive subject matter may be applied to various purposes or embodiments. Other embodiments are included within the inventive subject matter, as logical, mechanical, chemical, and other changes may be made to the example embodiments described herein. Features or limitations of various embodiments described herein, however essential to the example embodiments in which they are incorporated, do not limit the inventive subject matter as a whole, and any reference to the invention, its elements, operation, and application are not limiting as a whole, but serve only to define these example embodiments.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. 81.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

The invention claimed is:

1. A lip gloss comprising:
a sugar gel matrix that includes stearoyl inulin and an ester of formula R(1) COOR(2) in which R(1) is a residue of a fatty acid including from 6 to 29 carbon atoms and R(2) is a hydrocarbon-comprising chain comprising from 3 to 30 carbon atoms, entrapped in the stearoyl inulin sugar gel matrix;
a gel comprising hydrogenated polyisobutene; and
a gel comprising fumed silica dimethyl silicate in C(15-19) Hydrocarbon.

2. The lip gloss of claim 1, wherein diisostearyl malate is entrapped in the sugar gel matrix that includes stearoyl inulin.

3. The lip gloss of claim 1, wherein one or more of purcellin oil (cetostearyl octanoate), isopropyl myristate, 2-ethylhexyl palmitate, 2-octyldodecyl stearate, isostearyl isostearate, arachidyl propionate, 2-octyldodecyl benzoate; isostearyl lactate, octyl hydroxystearate, octyldodecyl hydroxystearate, triisocetyl citrate; propylene glycol dioctanoate, neopentyl glycol diheptanoate, diethylene glycol diisononanoate, pentaerythritol esters; octyidodecanol, 2-butyloctanol, 2-hexyldecanol, 2-undecylpentadecanol, oleyl alcohol, cetyl alcohol, isononyl isononanoate or C12-C15 alkyl benzoates, polyalkyl octanoates, decanoates ricinoleates, are entrapped in the sugar gel matrix that includes stearoyl inulin.

4. The lip gloss of claim 2, wherein the diisostearyl malate concentration is 0.05-20.00 percent by weight of the lip gloss.

5. The lip gloss of claim 1 wherein the stearoyl inulin concentration is 0.05-10.00 percent by weight.

6. The lip gloss of claim 1 wherein the C(15-19) hydrocarbon concentration is 10.00-25.00 percent by weight.

7. The lip gloss of claim 1 wherein the silica dimethyl silylate concentration is 1.00-10.00 percent by weight.

8. The lip gloss of claim 1, further comprising ethylene/propylene/styrene copolymer and butylene/ethylene/styrene copolymer.

9. The lip gloss of claim 8 wherein the hydrogenated polyisobutene and ethylene/propylene/styrenecopolymer and butylene/ethylene/styrene copolymer concentration is 25.00 percent by weight.

10. A lip gloss system, comprising:
a gel system comprising: sugar gel matrix that includes stearoyl inulin and an ester of formula R(1) COOR(2) in which R(1) is a residue of a fatty acid including from 6 to 29 carbon atoms and R(2) is a hydrocarbon-comprising chain comprising from 3 to 30 carbon atoms, entrapped in the stearoyl inulin sugar gel matrix;

a gel comprising hydrogenated polyisobutene;

a gel comprising fumed silica dimethyl silicate in C(15-19) Hydrocarbon; and packaging for packaging the gel system.

11. The lip gloss system of claim 10, wherein diisostearyl malate is entrapped in the sugar gel matrix that includes stearoyl inulin.

12. The lip gloss system of claim 10, wherein one or more of purcellin oil (cetostearyl octanoate), isopropyl myristate, 2-ethylhexyl palmitate, 2-octyldodecyl stearate, isostearyl isostearate, arachidyl propionate, 2-octyldodecyl benzoate; isostearyl lactate, octyl hydroxystearate, octyldodecyl hydroxystearate, triisocetyl citrate; propylene glycol dioctanoate, neopentyl glycol diheptanoate, diethylene glycol diisononanoate, pentaerythritol esters; octyidodecanol, 2-butyloctanol, 2-hexyldecanol, 2-undecylpentadecanol, oleyl alcohol, cetyl alcohol, isononyl isononanoate or $C_{12}$-$C_{15}$ alkyl benzoates, decanoates ricinoleates, are entrapped in the sugar gel matrix that includes stearoyl inulin.

13. The lip gloss system of claim 10, wherein the diisostearyl malate concentration is 0.05-20.00 percent by weight of the lip gloss.

14. The lip gloss system of claim 10 wherein the stearoyl inulin concentration is 0.05-20.00 percent by weight.

15. The lip gloss system of claim 10 wherein the C(15-19) hydrocarbon concentration is 10.00-25.00 percent by weight.

16. The lip gloss system of claim 10 wherein the silica dimethyl silylate concentration is 1.00-10.00 percent by weight.

17. The lip gloss system of claim 10, further comprising ethylene/propylene/styrene copolymer and butylene/ethylene/styrenecopolymer.

18. The lip gloss of claim 17 wherein the hydrogenated polyisobutene and ethylene/propylene/styrene copolymer and butylene/ethylene/styrenecopolymer concentration is 25.00 percent by weight.

* * * * *

UNITED STATES PATENT AND TRADEMARK OFFICE
CERTIFICATE OF CORRECTION

| | |
|---|---|
| PATENT NO. | : 8,236,289 B2 |
| APPLICATION NO. | : 12/140039 |
| DATED | : August 7, 2012 |
| INVENTOR(S) | : Nguyen et al. |

It is certified that error appears in the above-identified patent and that said Letters Patent is hereby corrected as shown below:

On the title page, in column 2, Item (56) under "Foreign patent Documents", line 4, In the citation for FOREIGN PATENT 22009035484, delete "22009035484" and insert --2009035484--, therefor Signed and Sealed this
Eleventh Day of November, 2014

Michelle K. Lee
*Deputy Director of the United States Patent and Trademark Office*